United States Patent
Oslund et al.

(10) Patent No.: US 8,298,160 B2
(45) Date of Patent: Oct. 30, 2012

(54) WIRE CONVERTIBLE FROM OVER-THE-WIRE LENGTH TO RAPID EXCHANGE LENGTH

(75) Inventors: John C. Oslund, Cottage Grove, MN (US); Patrick P. Russo, Vadnais Heights, MN (US)

(73) Assignee: EV3 Inc., Plymouth, MN (US)

( * ) Notice: Subject to any disclaimer, the term of this patent is extended or adjusted under 35 U.S.C. 154(b) by 943 days.

(21) Appl. No.: 10/100,686

(22) Filed: Mar. 14, 2002

(65) Prior Publication Data

US 2002/0133092 A1 Sep. 19, 2002

Related U.S. Application Data

(60) Provisional application No. 60/276,689, filed on Mar. 16, 2001.

(51) Int. Cl.
*A61B 5/00* (2006.01)
*A61M 25/00* (2006.01)

(52) U.S. Cl. ........ 600/585; 600/433; 600/434; 600/435; 604/164.13

(58) Field of Classification Search .......... 600/433–435, 600/585; 604/93.01, 164.13
See application file for complete search history.

(56) References Cited

U.S. PATENT DOCUMENTS

| | | | |
|---|---|---|---|
| 3,949,756 A * | 4/1976 | Ace | 606/227 |
| 4,501,065 A * | 2/1985 | Zemek et al. | 29/845 |
| 4,819,618 A | 4/1989 | Liprie | |
| 4,966,163 A * | 10/1990 | Kraus et al. | 600/585 |
| 5,024,659 A | 6/1991 | Sjostrom | |
| 5,109,867 A * | 5/1992 | Twyford, Jr. | 600/585 |
| 5,113,872 A * | 5/1992 | Jahrmarkt et al. | 600/585 |
| 5,122,136 A | 6/1992 | Guglielmi et al. | |
| 5,139,032 A | 8/1992 | Jahrmarkt et al. | |
| 5,139,500 A * | 8/1992 | Schwartz | 606/96 |
| 5,195,535 A * | 3/1993 | Shank | 600/585 |
| 5,195,978 A | 3/1993 | Schiffer | |
| 5,241,957 A * | 9/1993 | Camps et al. | 607/119 |
| 5,247,942 A * | 9/1993 | Prather et al. | 600/585 |
| 5,441,055 A * | 8/1995 | Ales et al. | 600/585 |
| 5,465,733 A * | 11/1995 | Hinohara et al. | 600/585 |
| 5,507,729 A * | 4/1996 | Lindenberg et al. | 604/170.01 |
| 5,511,559 A * | 4/1996 | Vance | 600/585 |
| 5,607,406 A * | 3/1997 | Hernandez et al. | 604/264 |
| 5,666,968 A * | 9/1997 | Imran et al. | 600/585 |
| 5,701,911 A * | 12/1997 | Sasamine et al. | 600/585 |
| 5,733,248 A * | 3/1998 | Adams et al. | 600/585 |
| 5,759,161 A | 6/1998 | Ogawa et al. | |
| 5,813,405 A | 9/1998 | Montano, Jr. et al. | |
| 5,846,210 A | 12/1998 | Ogawa et al. | |
| 5,902,310 A * | 5/1999 | Foerster et al. | 606/142 |

(Continued)

FOREIGN PATENT DOCUMENTS

EP 0 815 892 A1 1/1998

(Continued)

*Primary Examiner* — Rene Towa

(74) *Attorney, Agent, or Firm* — Alana T. Bergman

(57) ABSTRACT

Apparatus for use in deploying medical devices. The apparatus includes a wire having a diameter such that the wire can appropriately be used with either a corresponding over-the-wire configured catheter or a rapid-exchange configured catheter. The wire has a location at which it can be easily fractured, when desired, in order to convert the length of the wire from a length for use in an over-the-wire configuration to a rapid-exchange configuration.

20 Claims, 1 Drawing Sheet

U.S. PATENT DOCUMENTS

| | | | |
|---|---|---|---|
| 6,022,369 A * | 2/2000 | Jacobsen et al. | 606/191 |
| 6,193,706 B1 * | 2/2001 | Thorud et al. | 604/533 |
| 6,290,656 B1 * | 9/2001 | Boyle et al. | 600/585 |
| 6,360,130 B1 * | 3/2002 | Duysens et al. | 607/132 |
| 6,387,060 B1 * | 5/2002 | Jalisi | 600/585 |
| 6,428,489 B1 * | 8/2002 | Jacobsen et al. | 600/585 |
| 2003/0105484 A1 | 6/2003 | Boyle et al. | |

FOREIGN PATENT DOCUMENTS

| | | |
|---|---|---|
| WO | WO 03/047461 | 6/2003 |

* cited by examiner

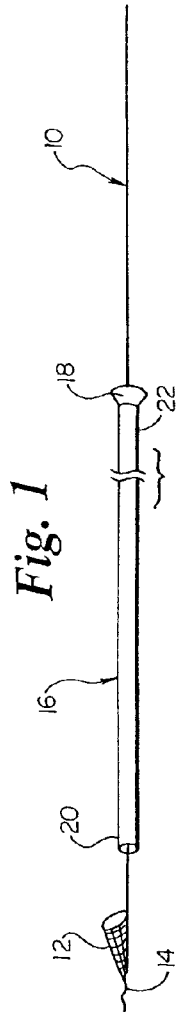
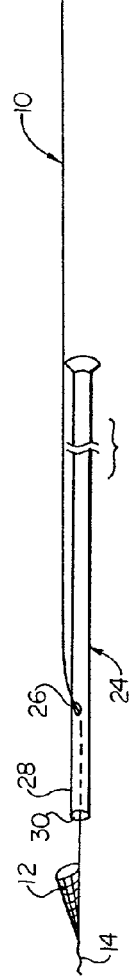
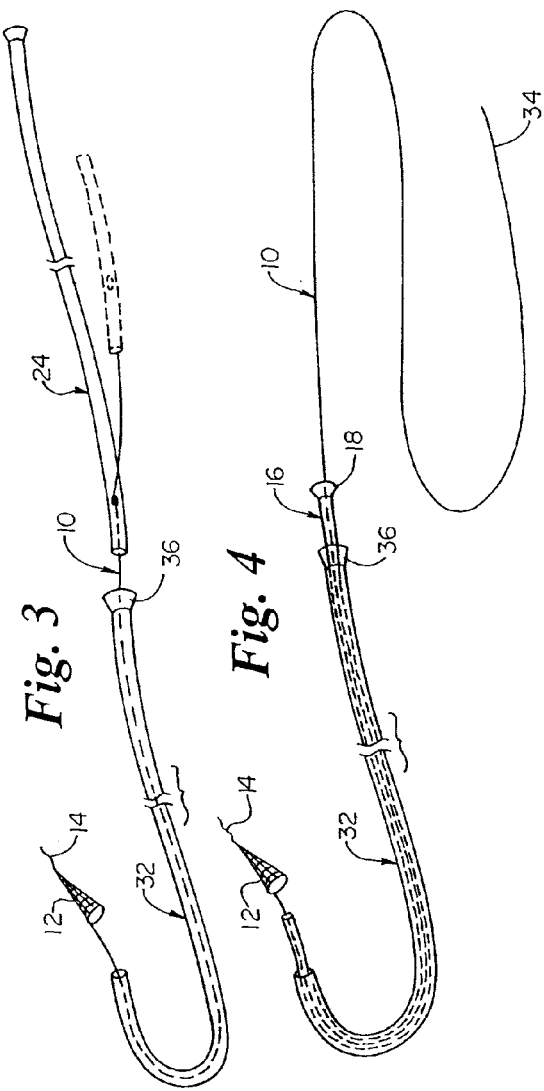
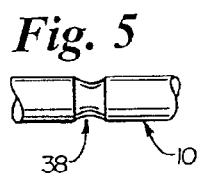
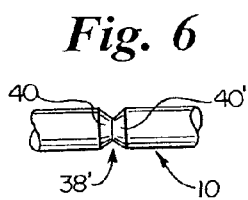
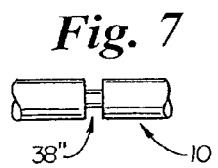

WIRE CONVERTIBLE FROM OVER-THE-WIRE LENGTH TO RAPID EXCHANGE LENGTH

This application claims the benefit of provisional application Ser. No. 60/276,689, filed Mar. 16, 2001.

BACKGROUND OF THE INVENTION

1. Field of the Invention

The present invention relates generally to wires for use in medical procedures. More specifically, the present invention relates to guidewires and hostwires capable of being converted from an over-the-wire length to a rapid-exchange length.

2. Description of the Prior Art

Guidewires are generally elongate structures for use in medical procedures. During such procedures, a distal portion of the wire is positioned within a lumen of a patient's body to acquire and/or maintain access to a treatment site. Commonly, such a lumen of a patient's body includes a stenosed region at a location in the patient's vascular system. A catheter can be advanced over a wire for treatment or diagnostic purposes.

The wire and catheter are positioned within the patient's body by an operator such as a medical doctor. A proximal portion of the wire and a proximal portion of the catheter extend outwardly from the patient's body for manipulation by the operator. In the case of over-the-wire systems, at least a portion of the wire must extend proximally relative to the proximal end of the catheter, thereby allowing the catheter to be manipulated axially relative to the wire.

Distal protection devices are devices that protect tissue downstream in a patient's vascular system from emboli arising during medical procedures. Distal protection devices may be filters or may be occlusive, and are deployed distal to a treatment site. The filter or occlusive element is mounted to a hostwire. Hostwires have some functions similar to guidewires in that catheters are commonly advanced over both to or near treatment sites.

Guidewires and hostwires may be maintained at an intended axial position within the lumen of the patient's body so as to afford access to a treatment site, as desired. The wire may be maintained by any means that enable the relative position of the wire to be established within the lumen, such as by an anchored distal protection device, or by manually maintaining the position of the wire within the lumen. Once an axial position is established, the wire is maintained in position to allow treatment and diagnostic devices such as a percutaneous transluminal coronary angioplasty (hereinafter referred to as "PTCA") balloon catheter, a stent, or the like to be advanced over the wire to the treatment site.

During a procedure, the operator must be able, when necessary, to manipulate the catheter and wire relative to each other. Thus, as previously discussed, for over the wire systems, the wire must have a greater length than the receiving lumen of the catheter in order for the operator to be able to maintain access to the wire independently of the catheter during catheter exchanges. Typically, these wires are over 300 cm in length.

Two types of wire/catheter configurations are commonly employed: an "over-the-wire" configuration and a "rapid-exchange" configuration. In an "over-the-wire" configuration, the wire is used with an over-the-wire catheter comprising an elongate body having a lumen extending the length of the catheter. The over-the-wire catheter is advanced relative to the wire by sliding the wire through the lumen. Again, in order for the operator to position the over-the-wire catheter with respect to the wire, a portion of the wire must extend from the patient's body and out of the proximal end of the over-the-wire catheter.

A rapid-exchange catheter has an elongate structure, only a distal portion of which defines a used region having a receiving lumen for receiving the wire. The receiving lumen of a rapid-exchange catheter is typically considerably less than half the overall length of the rapid-exchange catheter. Thus, the wire, in order to extend from the patient's body, need only be longer than the appropriate length of the receiving lumen of the rapid-exchange catheter and the length of the vascular passage from a point of body ingress to a port in the catheter through which the wire enters the receiving lumen. Typically, these wires are about 175 cm in length. The operator is, therefore, able to manipulate the catheter with respect to the wire with a much shorter wire length. The result is that the length of the wire in a rapid-exchange configuration can be significantly less than the length of an over-the-wire wire.

During the course of a procedure, a plurality of devices may be advanced over the wire. The devices may be for use in an over-the-wire configuration or a rapid-exchange configuration. An over-the-wire system configuration generally provides more support to the catheter and has superior lesion crossing abilities, especially in tortuous anatomy. A rapid-exchange catheter is generally easier for the operator to use and may require less assistance during operation relative to an over-the-wire catheter. The length of the wire, again, depends on the type of catheter configuration that will be employed. It is not, however, always known in advance whether an over-the-wire length or a rapid-exchange length wire will be required.

Because of the possibility that a combination of rapid-exchange and over-the-wire length catheters will need to be employed, rapid-exchange length guidewires that are extendable to an over-the-wire length for receiving over-the-wire length catheters have come to be employed.

The superior crossing ability of over-the-wire systems coupled with the ease of use of a rapid-exchange guidewire or hostwire, however, makes it beneficial to have an over-the-wire length guidewire or hostwire that can be transformed into a guidewire or hostwire capable of use in a rapid-exchange configuration. A convertible wire would allow the operator to position and anchor the wire within a lumen of a patient's vasculature using an over-the-wire catheter and then convert the wire to a rapid-exchange length, as needed, for use with rapid-exchange catheters during the same procedure. This would eliminate the need for the manufacture of separate wire assemblies for use with rapid-exchange catheters and over-the-wire catheters.

SUMMARY OF THE INVENTION

The present invention is a medical apparatus for use in deploying various interventional devices. Such devices typically include PTCA balloon catheters, stents, catheters for use with distal protection devices, etc. The apparatus comprises an elongate wire having a given diameter. The diameter of the wire selected is one which is appropriate in view of an initial catheter with which it is intended to be used. The apparatus can be used with either of corresponding over-the-wire or rapid-exchange configured catheters. The elongate wire has a length appropriate for use with the corresponding over-the-wire configured catheter. The wire is provided with a defined location of frangibility. The location of frangibility is defined at an axial point along the wire such that, when the wire is fractured at the defined location of frangibility, the wire assumes a length appropriate for use with a corresponding rapid-exchange catheter. While the wire with which the present invention is used can be a guidewire, in a preferred embodiment, the wire is a hostwire for a distal protection device.

In a preferred embodiment, the location of frangibility is made such that, when the wire is subjected to an appropriate degree of arcuate bending, the wire will fracture at the location of frangibility.

In an embodiment of the invention, the location of frangibility is defined by an annular scored portion. The scored portion can be formed in one of a number of configurations. In the preferred embodiment, the scored portion comprises an axially concave recess. The concavity has a diameter which, at its narrowest, is approximately 25% less than the diameter of the elongate wire itself.

In other embodiments, the annular scored portion can take other forms. For example, it can comprise a uniform diameter recess, that uniform diameter being less than the overall diameter of the elongate wire. Here again, the reduction in diameter would be approximately 25% of that of the diameter of the overall wire.

Another embodiment envisions an inwardly tapering recess defined by a pair of truncated conical segments having similar minor diameters. In this embodiment, the minor diameters of the truncated conical segments are in engagement with one another. There is, therefore, uniform inward tapering from opposite directions.

In still other embodiments the location of frangibility is produced by localized heat or chemical treatment.

Typically, the normal length of the elongate wire, when used in an over-the-wire configuration, is within the range of 300 cm to 340 cm. A desired length of a wire for use in a rapid-exchange configuration is within the range of between 160 cm and 200 cm. The annular scored portion is, therefore, typically provided at a distance of approximately 180 cm from a distal end of the elongate wire.

Irrespective of the manner in which a location of frangibility is provided and the specific length of wire involved, the wire can be coded by some manner of marker identification as to where the location of frangibility is. Such coding facilitates quick identification of the location of frangibility to the operator and enables ease of use of the wire. This is particularly important in view of lighting conditions and other factors which would otherwise diminish the ability of the operator to quickly and efficiently effect fracturing of a wire. Such marking can take the form of coding, with contrasting color portions being given to opposite sides of the defined location of frangibility. The specific area at which frangibility exists can further be identified by an easily perceivable band of color such as white.

The present invention is thus an improved apparatus for use in deploying medical devices such as PTCA balloon catheters, stents, catheters for use with distal protection devices, etc. More specific features and advantages obtained in view of those features will become apparent with reference to the DETAILED DESCRIPTION OF THE INVENTION and the appended claims.

BRIEF DESCRIPTION OF THE DRAWING FIGURES

FIG. 1 is a side elevational view of a wire configured for use with an over-the-wire delivery catheter;

FIG. 2 is a side elevational view of a wire configured for use with an rapid-exchange delivery catheter;

FIG. 3 is a view illustrating the catheter configuration of FIG. 2 as used in combination with a guide catheter;

FIG. 4 is a view illustrating the catheter configuration of FIG. 1 as used in combination with a guide catheter;

FIG. 5 illustrates a segment of a wire in accordance with the present invention showing one embodiment of a defined location of frangibility;

FIG. 6 is a view similar to FIG. 5 showing an alternative embodiment of the defined location of frangibility; and FIG. 7 is a view similar to FIGS. 5 and 6 showing another alternative embodiment of the defined location of frangibility.

DETAILED DESCRIPTION OF THE INVENTION

Referring now to the drawing figures wherein like reference numerals denote like elements throughout the several views, FIG. 1 illustrates a hostwire 10 having a trap device 12 mounted proximate its distal end 14. The trap device 12 is shown as being deployed from a delivery catheter 16 constructed in an over-the-wire configuration. The delivery catheter 16 is shown as having, at its proximal end, a portion which tapers inwardly in a distal direction. The flared wall 18 thereby formed facilitates feeding of a wire into and through the delivery catheter 16. The distal protection device or trap 12 is, prior to deployment from the delivery catheter 16, held in a compressed state within the delivery catheter 16. Again, however, FIG. 1 illustrates the distal protection device 12 as having been urged distally with respect to the delivery catheter 16 so that it has assumed a deployed configuration.

FIG. 1 illustrates a need for the hostwire 10 to be at least as long as the delivery catheter 16. The hostwire 10 must extend in excess of the full length of the delivery catheter 16 so that the distal protection device 12 can be deployed from the distal end of the catheter 16, and so that the operator can grasp the wire 10 proximal to the catheter 16 to assist in manipulating the protection device 12. The wire 10, in order to be able to accomplish this, must be long enough to extend from both the distal end 20 and the proximal end 22 of the catheter 16 at the same time.

FIG. 2 illustrates the wire 10 mounting a distal protection device or trap 12 proximate its distal end 14, and as used in combination with a rapid-exchange catheter 24. The construction of the delivery catheter 24 for use in the rapid-exchange mode is similar to the over-the-wire catheter 16, but a port 26 is formed in the wall of the rapid exchange catheter 24 proximate the distal end 28 thereof. The hostwire 10 is able, therefore, to be fed in a proximal direction into the distal end 28 of the catheter 24, through the lumen 30 of the catheter 24 rapid-exchange segment, out through the port 26, and external to the catheter wall. As a result of the run of the wire 10 external to the wall defining the catheter lumen 30, the wire 10 is accessible from the catheter 24 at a point much more distal than it would be in the case of the over-the-wire configuration. Consequently, the wire 10 can have a much shorter length in the rapid-exchange configuration.

FIG. 4 illustrates an over-the-wire catheter configuration as also shown in FIG. 1. In FIG. 4, however, the delivery catheter 16 has been fed through a guide catheter 32 in place in a lumen of a patient's body (not shown). To remove the over-the-wire catheter 16 from the wire 10, the catheter 16 is withdrawn proximally over the wire 10 while the operator holds the proximal end 34 of the wire 10 stationary, until the distal end 20 of the delivery catheter 16 is withdrawn proximal to the proximal end 36 of the guide catheter 32. At this point the operator holds the wire 10 stationary by grasping the wire 10 immediately proximal to the guide catheter, and removes the catheter from the wire by withdrawing the delivery catheter 16 proximally off of the stationary held wire 10. As suggested by this procedure, the hostwire length must exceed the length of the guide catheter 32 plus the length of the delivery catheter 16.

FIG. 3 illustrates a hostwire 10 in combination with a rapid-exchange configured catheter 24. FIGS. 2 and 3 illustrate an assembly that renders the wire 10 such that it can be considerably shorter as used in a rapid-exchange catheter configuration than when used in an over-the-wire configuration. To remove the rapid exchange catheter 24 from the wire 10, the catheter 24 is removed using the same procedure as described in connection with FIG. 4. The rapid-exchange procedure requires that the hostwire length exceed the length of the guide catheter 32 plus the length of the rapid exchange segment.

The present invention, in order to facilitate optimization of length of the hostwire, depending upon the particular catheter configuration utilized, is manufactured so as to be frangible at a defined location therealong. While a typical range of lengths for an over-the-wire configuration would be between 300 cm and 340 cm (and particularly 320 cm), a typical desired length range for the wire used in a rapid exchange configuration is between 160 cm and 200 cm (and particularly 180 cm). Consequently, the present invention envisions providing a wire of between 300 cm and 340 cm in length with a frangible portion defined therealong somewhere between 160 cm and 200 cm from the distal end of the wire.

FIGS. 5-7 illustrate three different embodiments of a hostwire structure having a defined location of frangibility formed therein. In each case shown, the location of frangibility is defined by an annular scored portion 38, 38', 38". The score in the wire can be made by chemical etching, laser cutting, EDM, grinding, coining or any other appropriate cutting method. It will be understood that the location of frangibility can also be defined other than by physically notching the wire. For example, the location of frangibility could be created by using localized heat treatment at the location on the wire where the frangibility is desired. Further, the location of frangibility could be created by using a combination of these methods (for example, scoring and heat treating).

It will be understood that it is not necessary for a physically notched location of frangibility to be annular, and the notch may not traverse the entire wire circumference. It will further be understood that the location of frangibility is constructed to be able to break in a smooth and burr-free manner, free of sharp edges that could damage doctors' gloves or that could damage or result in resistance on passage through a catheter lumen.

To some extent, the method of defining the location of frangibility will vary in view of the type of wire that is being used. Metallic wires are, of course, appropriate, but other materials can also be used. Other examples are ceramic materials, composites including carbon or glass fiber, any stiff polymer material such as polyether ketone (PEEK), liquid crystal polymer, polyimide, and the like, with or without metal or ceramic reinforcement. It will be understood that any material presently used for manufacturing such wires should be appropriate. Again, the method of defining the location of frangibility can vary depending upon the material of which the wire is made, and the degree of compatibility of material with the particular process will govern.

FIG. 5 illustrates an annular scored portion 38 taking the form of an axially concave, annular recess. In this embodiment, it is desirable that the smallest measurable diameter within the recess be in a range between 5% and 60%, and approximately 25%, reduced from the normal diameter of the wire.

FIG. 6 illustrates another physically notched location of frangibility 38'. In this embodiment, the wire is formed so that a pair of truncated conical segments 40, 40' are defined. Each segment has a minor diameter similar to the minor diameter of the other segment. Such similar minor diameters are adjacent to one another. Such a notch 38' is, thereby, formed by two segments tapering inward in opposite axial directions. Again, it is desirable that the smallest reduced diameter be in a range between 5% and 60%, and approximately 25%, smaller than the normal diameter of the wire.

FIG. 7 illustrates a third physically reduced diameter defining the annular scored portion 38". That figure illustrates a recess having a uniform reduced diameter. Again, it is desirable that the reduced diameter be in the range between 5% and 60%, and approximately 25%, smaller than the normal diameter of the wire.

Regardless of how the location of frangibility is defined, however, the frangibility location is constructed so as to stand up to normal wire use. Such normal use includes pushing, pulling and coiling operations. Commonly the wire must survive handling and mishandling in a catheter lab environment. It is, of course, undesirable that the wire break other than when the operator desires to effect fracture. Therefore, the wire is constructed to break only when the operator intends to stress the location of frangibility in a manner greater than what the wire sees during normal use.

To facilitate fracture of the wire, marking can be employed to identify to the operator where the location of frangibility is. This would be true irrespective of the manner in which the location of frangibility is defined. Because of the very small diameters involved, it may be difficult to see a notch, even when such physical means are used to define the location of frangibility. This result can occur because of poor lighting conditions, blood contamination and other factors.

Consequently, coding can be employed. The color of the wire on one side of the location of frangibility can be such that it is made to contrast with the color of the wire on the other side. If desired, the specific location of frangibility can be accentuated by making it a very conspicuous color. For example, there might be a white band at the specifically defined location of frangibility.

In using the inventive apparatus, the operator pre-loads a primary guidewire into a catheter configured in an over-the-wire manner. The delivery catheter is then inserted into a guide catheter 32 previously installed by way, typically, of the femoral artery and the aorta. A stenosis located in a coronary artery which is to be treated is crossed with the primary guidewire. The delivery catheter is then advanced over the guidewire to a location beyond the stenosis. The primary guidewire is then withdrawn from the delivery catheter with the distal end of that catheter at a location beyond the stenosis.

Alternatively, the stenosis can be crossed with an over-the-wire length guidewire, and the catheter advanced over the over-the-wire length guidewire and across the stenosis. At this point, the over-the-wire length guidewire is withdrawn from the catheter.

A distal protection device 12, for example, attached to a hostwire with a location of frangibility is front-loaded through the delivery catheter. The distal protection device 12 can, thereby, be deployed at a location distal to the treatment region. With the distal protection device thus deployed, the delivery catheter is then removed from the hostwire in an over-the-wire fashion.

At this point in the procedure, the operator has the option of retaining the hostwire 10 at an over-the-wire length. This would be done if the operator chooses to perform an intervention using over-the-wire devices.

The operator does, however, have the option of performing the intervention using rapid-exchange devices. If such an option is chosen, the hostwire 10, configured in accordance with the present invention with a location of frangibility, is fractured at that location and converted to a rapid-exchange length wire. The proximal portion of the separated wire is discarded.

Thereafter, all interventions, such as PTCA or stenting, are performed in a rapid exchange configuration. The distal protection device is ultimately recovered using a rapid exchange recovery catheter. Such a recovery catheter can be used regardless of whether or not the hostwire has been fractured to the shorter length.

In an alternate use, the distal protection device with the location of frangibility is placed distal to a stenosis as described above. The delivery catheter can be withdrawn until the distal end of the delivery catheter is immediately proximal to the location of frangibility. At this point, the hostwire can be broken and the delivery catheter, with proximal portion of the frangible wire therein, can be set aside or discarded.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. An assembly for use by an operator in performing a medical procedure in a lumen of a patient comprising an over-the-wire configured catheter and a wire for use in deploying the over-the-wire configured catheter, the wire comprising:

an elongate cylindrical body having a distal end, a proximal end and a location of fracturability, the elongate cylindrical body being formed from a single continuous piece of material having a cross-sectional shape defined by the intersection of the elongate cylindrical body with a plane perpendicular to an axis of the elongate cylindrical body, the cross-sectional shape being substantially constant between the proximal end and the location of fracturability and between the distal end and the location of fracturability;

a full length of the elongate cylindrical body defined from the distal end to the proximal end, a partial length of the elongate cylindrical body defined from the distal end to the location of fracturability, the elongate cylindrical body being configured to fracture outside of the lumen at the location of fracturability upon application by the operator to the elongate cylindrical body of a sufficient amount of bending stress, the sufficient amount of bending stress being selected to be greater than a maximum bending stress to which the elongate cylindrical body is subjected during the medical procedure within the lumen, and less than an amount of bending stress required to fracture the elongate cylindrical body at portions of the elongate cylindrical body proximally and distally adjacent to the location of fracturability;

wherein the partial length of the elongate cylindrical body is within a range of between 160 centimeters and 200 centimeters.

2. An assembly of claim 1, wherein the partial length of the elongate cylindrical body is substantially 180 centimeters.

3. An assembly of claim 1, wherein the full length of the elongate cylindrical body is substantially 320 centimeters.

4. An assembly of claim 1, wherein said location of fracturability is defined by an axially concave recess.

5. An assembly of claim 1, wherein said location of fracturability is defined by a uniform diameter recess having a diameter less than a diameter of said elongate cylindrical body.

6. An assembly of claim 1, wherein said location of fracturability is defined by a recess formed by a pair of truncated conical segments having similar minor diameters thereof in engagement with one another.

7. An assembly of claim 1, wherein said wire is a guidewire.

8. An assembly of claim 1, wherein said wire is a hostwire.

9. An assembly of claim 8, wherein a distal protection device is mounted proximate the distal end of the fracturable elongate cylindrical body.

10. An assembly of claim 1, wherein the assembly further comprises a guide catheter.

11. An assembly for use by an operator in performing a medical procedure in a lumen of a patient comprising a rapid-exchange configured catheter and a wire for use in deploying the rapid-exchange configured catheter, the wire comprising:

an elongate cylindrical body having a distal end, a proximal end and a location of fracturability, the elongate cylindrical body being formed from a single continuous piece of material having a cross-sectional shape defined by the intersection of the elongate cylindrical body with a plane perpendicular to an axis of the elongate cylindrical body, the cross-sectional shape being substantially constant between the proximal end and the location of fracturability and between the distal end and the location of fracturability;

a full length of the elongate cylindrical body defined from the distal end to the proximal end, a partial length of the elongate cylindrical body defined from the distal end to the location of fracturability, the elongate cylindrical body being configured to fracture outside of the lumen at the location of fracturability upon application by the operator to the elongate cylindrical body of a sufficient amount of bending stress, the sufficient amount of bending stress being selected to be greater than a maximum bending stress to which the elongate cylindrical body is subjected during the medical procedure within the lumen, and less than an amount of bending stress required to fracture the elongate cylindrical body at portions of the elongate cylindrical body proximally and distally adjacent to the location of fracturability;

wherein the partial length of the elongate cylindrical body is within a range of between 160 centimeters and 200 centimeters.

12. An assembly of claim 11, wherein the partial length of the elongate cylindrical body is substantially 180 centimeters.

13. An assembly of claim 11, wherein the full length of the elongate cylindrical body is substantially 320 centimeters.

14. An assembly of claim 11, wherein said location of fracturability is defined by an axially concave recess.

15. An assembly of claim 11, wherein said location of fracturability is defined by a uniform diameter recess having a diameter less than a diameter of said elongate cylindrical body.

16. An assembly of claim 11, wherein said location of fracturability is defined by a recess formed by a pair of truncated conical segments having similar minor diameters thereof in engagement with one another.

17. An assembly of claim 11, wherein said wire is a guidewire.

18. An assembly of claim 11, wherein said wire is a hostwire.

19. An assembly of claim 18, wherein a distal protection device is mounted proximate the distal end of the fracturable elongate cylindrical body.

20. An assembly of claim 11, wherein the assembly further comprises a guide catheter.

* * * * *